United States Patent [19]

Le Cleac'h et al.

[11] Patent Number: 5,049,812

[45] Date of Patent: Sep. 17, 1991

[54] DEVICE FOR THE ELECTRIC CHARACTERIZATION OF SAMPLES AND APPLICATION TO ELECTRIC MAPPING OF LARGE AREA SEMICONDUCTOR SAMPLES

[75] Inventors: Xavier Le Cleac'h, Trelevern; Pierre-Noël Favennec, Lannion, both of France

[73] Assignees: French State, represented by the Minister of Post, Telecommunications and Space (Centre National D'Etudes Des Telecommunications), Issy Les Moulineaux; Universite de Rennes, Rennes, both of France

[21] Appl. No.: 490,558

[22] PCT Filed: Nov. 16, 1988

[86] PCT No.: PCT/FR88/00563

§ 371 Date: May 9, 1989

§ 102(e) Date: May 9, 1989

[87] PCT Pub. No.: WO89/04969

PCT Pub. Date: Jun. 1, 1989

[30] Foreign Application Priority Data

Nov. 17, 1987 [FR] France .............................. 87 15858

[51] Int. Cl.⁵ .............................................. G01R 1/04
[52] U.S. Cl. .............................. 324/158 R; 324/158 P; 324/717; 324/718
[58] Field of Search ............... 324/609, 619, 636, 637, 324/605, 639, 713, 715, 717, 718, 158 R, 158 D; 333/246

[56] References Cited

U.S. PATENT DOCUMENTS

| | | |
|---|---|---|
| 3,136,946 | 6/1964 | Le Vine . |
| 3,508,145 | 4/1970 | Reed et al. . |
| 3,942,107 | 3/1976 | Gerhard .............................. 324/690 |
| 4,123,703 | 10/1978 | Robinson . |
| 4,190,799 | 2/1980 | Miller et al. ..................... 324/158 D |
| 4,220,915 | 9/1980 | Kawamoto et al. ................ 324/717 |
| 4,543,576 | 9/1985 | Hieber et al. ................... 340/870.17 |
| 4,605,893 | 8/1986 | Braslau ........................... 324/158 P |
| 4,621,233 | 11/1986 | Davari et al. ..................... 324/158 R |
| 4,823,073 | 4/1989 | Schober ............................... 324/717 |
| 4,833,396 | 5/1989 | Haberland ........................... 324/718 |
| 4,841,224 | 6/1989 | Chalupnik et al. ................. 324/609 |
| 4,866,370 | 9/1989 | Flemming et al. .................. 324/639 |
| 4,891,584 | 1/1990 | Kamienicki et al. ......... 324/158 D |
| 4,896,096 | 1/1990 | Ewart ................................... 324/637 |

FOREIGN PATENT DOCUMENTS 1372886 10/1967 France .

OTHER PUBLICATIONS

"Contactless Semiconductor Mobility Determination", by Braslau, IBM Tech. Disc. Bull., vol. 27, #9, 2/85, pp. 5078-5080.

"The Study of Change Carrier Kinetics in Semiconductors by Microwave Conductivity Measurements", by Kunst et al., J. Appl. Phys. 60(10), 11/86, pp. 3558-3566.

Primary Examiner—Kenneth A. Wieder
Assistant Examiner—William J. Burns
Attorney, Agent, or Firm—Larson and Taylor

[57] ABSTRACT

A device for the electric characterization of samples, comprises a UHF resonator intended to be coupled locally to the sample. The resonator is formed by a microstrip or triplate line loop (20) carried by a conducting plane (16) and having a gap of small length with respect to the length of the loop and an assembly (32) for receiving the sample in a position in which the sample is coupled selectively to the edges of the gap without being interposed therebetween. The edges of the gap of the loop are fixed to two electrodes of small area passing through a thin plate of dielectric material having a flat face for application against the sample.

9 Claims, 2 Drawing Sheets

DEVICE FOR THE ELECTRIC CHARACTERIZATION OF SAMPLES AND APPLICATION TO ELECTRIC MAPPING OF LARGE AREA SEMICONDUCTOR SAMPLES

The present invention relates to devices for the electric characterization of samples and is more particularly applicable to electric mapping of semiconductor samples of large area, in solid or thin layer form. It relates more particularly to the devices for determining the electric conductivity $\sigma$ (or surface resistance) and/or the mobility $\mu$ of carriers in the semiconductor material.

Numerous devices are already known for measuring $\sigma$ and $\mu$. Among the non destructive methods, several use closed cavities working in the UHF range. But these solutions are either only applicable to small sized samples, usually less than $5 \times 5$ mm$^2$ (X. LE CLEAC'H, rev. Phys. Appl. 17 (1982) pages 481–490) or have only very poor resolution and do not allow a sample to be characterized locally, for it must completely close the end of a wave-guide.

Contactless electric mapping devices are further known which do not use the UHF technique but detection of eddy currents or a Hall voltage. Although this solution (HORIGUCHI et al., Japan Appl. 18, suppl. 18-1 pages 165–171) makes local analysis possible, it has different drawbacks. Since the measurement of $\mu$ takes place using a metal disk and ring forming capacitors with the sample at a very small distance (about 10$\mu$), any variation of distance causes an error which may be considerable in the measurement of $\mu$. It is difficult to effect automatic mapping, for manual adjustments are required during experimentation. Finally, the use of eddy currents makes the method unusable when the surface conductivity of the sample is too low, in practice when the squared resistance R exceeds 500 ohms.

The object of the present invention is to provide a device for the electric mapping of samples, of the type using UHF frequencies, answering better than those known heretofore the requirements of practice, particularly in that it makes high resolution possible on a sample which may be of a large area, and in that it is applicable even in the case where the conductivity of the sample is low.

To this end, the invention provides particularly a device comprising a UHF resonator for coupling locally to the sample, characterized in that the resonator is formed by a microstrip or triplate line loop carried by a conducting plane and having a gap of small length with respect to the length of the loop, the edges of the gap being formed so as to permit selective coupling thereof to the sample of material to be studied. With such a device, measurements can be made which are of a kind very different from each other.

In particular, it makes possible electric conductivity mapping of thin layer or solid state semiconductor samples; it also makes possible electric mobility magnetoresistance mapping of semiconductor samples. It also makes possible photoconductance mapping of semiconductor or semi-insulating samples. For that, in the conducting plane and insulator of the line, a passage is formed opening into the gap for sending a light beam on to the sample.

The device can be adapted to surface mapping of semiconductor material, either solid or in thin layer form, for example implanted or epitaxied.

In an advantageous embodiment of the invention, the edges of the gap of the loop are fixed to two electrodes of small area passing through a thin plate of dielectric material having a flat face intended to be applied against the sample. When a device of this kind is to be used for surface homogeneity mapping by photoconductance, the passage formed in the conducting plane and the dielectric of the line opens between the electrodes.

The part of the loop remote from the edges of the gap will generally be at a distance from the surface of the thin plate applied on the sample greater than that of the edges which are fixed directly to the electrodes deposited on the plate. Thus, the high coupling zone between the sample and the loop is limited to the zone immediately surrounding the gap.

The UHF resonator is provided for coupling to a UHF generator and a detector. Lead-in and lead-out microstrips may in particular be provided having low coupling with portions of the loop remote from the gap. The generator will usually be provided for feeding the loop at a frequency corresponding to resonance of the latter in the absence of samples.

The invention will be better understood from the following description of particular embodiments, given by way of non limitative example. The description refers to the accompanying drawings in which:

FIG. 1 is a simplified diagram showing in a top view the construction of a microstrip resonator for a device according to the invention;

FIG. 2. is a sectional view through line II-II of FIG. 1;

Figure 1:
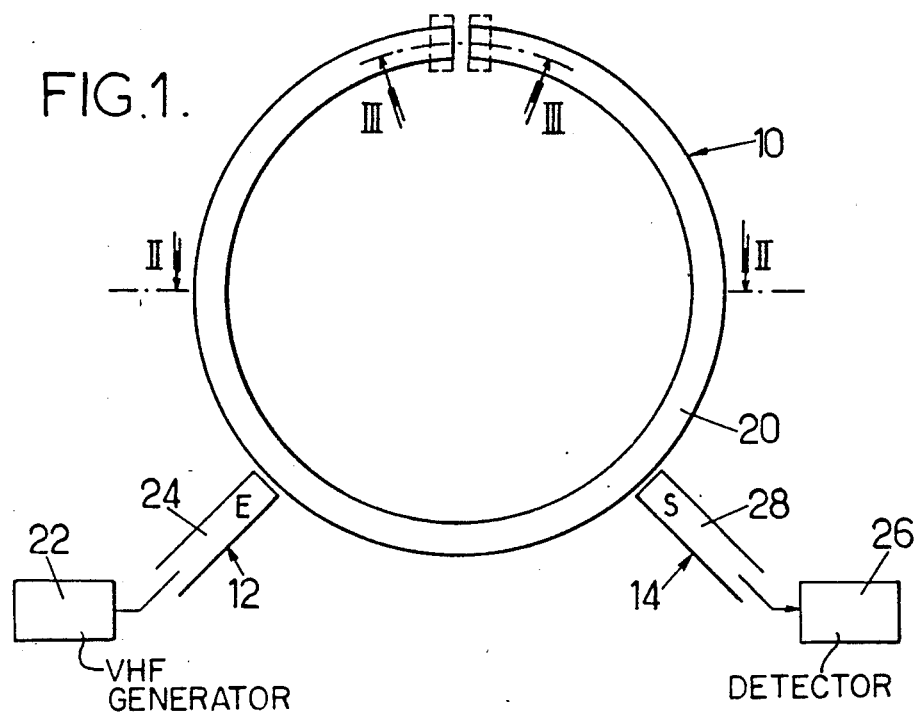
Figure 2:
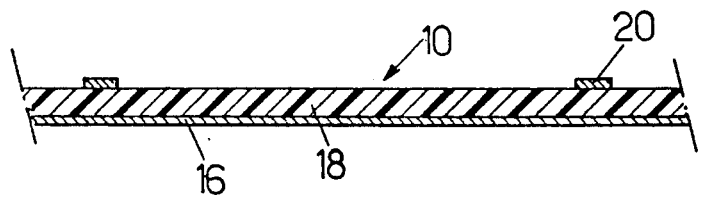

The device shown schematically in FIGS. 1 and 2 can be used more particularly for the mapping of a semiconductor sample whose surface resistivity R$_\square$ may range from 50 to 10$^4$ ohms and whose mobility exceeds $$500 \text{ cm}^2.\text{v}^{-1}.\text{s}^{-1},$$

with a resolution which may go down as far as 2 mm in each direction. This resolution may be brought to 0.25 mm$^2$ when the device is used for the mapping of surface homogeneities of a sample by photoconductance, by adapting the device as will be described further on.

The device shown in FIG. 1 may be regarded as comprising a measuring cell 10, power supply means 12 and measuring means 14. The basic element of the measuring cell is formed by a microstrip resonator in the form of a metal ground plane 16 covered by a dielectric layer 18 carrying the microstrip line 20. This line is in the form of a ring having a gap of small length compared with the length of the loop. In practice, the ground plane may be formed by a copper sheet a few tens of microns thick; the dielectric layer 18 is for example made from silica or a synthetic material (such as polytetrafluoroethylene and the glass "TEFLON"). The microstrip line properly speaking may have a width of about 5 mm. The gap will generally have a width less than a millimeter, e.g. 0.5 mm.

The power supply means 12 comprise an UHF generator 22 driving the resonator through a microstrip 24 having low coupling with the resonator. This generator 22 will in general be provided for working at a frequency between 100 MHz and 6 GHz. The measuring means 14 comprise a detector 26 connected to a microstrip 28 having, like microstrip 24, low coupling with a zone of the loop distant from the gap.

The length of the ring line determines the resonance frequencies of the resonator, which correspond to ring lengths equal to an uneven multiple of the half wavelength λ. At resonance, the electric signals which arrive simultaneously at both edges of the gap are in phase opposition.

The zone of the sample to be studied is situated above the gap. It is desirable for the electromagnetic interactions between the loop and the sample, which must be of a large area, to be localized in the zone of the gap, where the electric field is fairly uniform.

Figure 3:
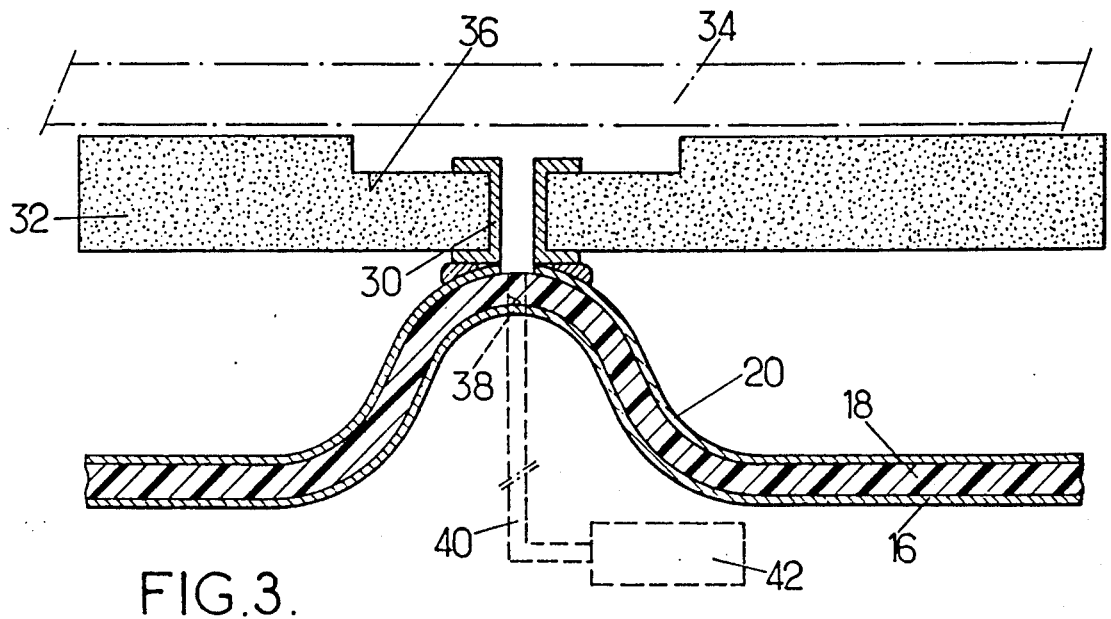
FIG. 3 is a large scale representation of the detection zone of a microstrip resonator according to the invention, in section through line III-III of FIG. 1.
Figure 4:
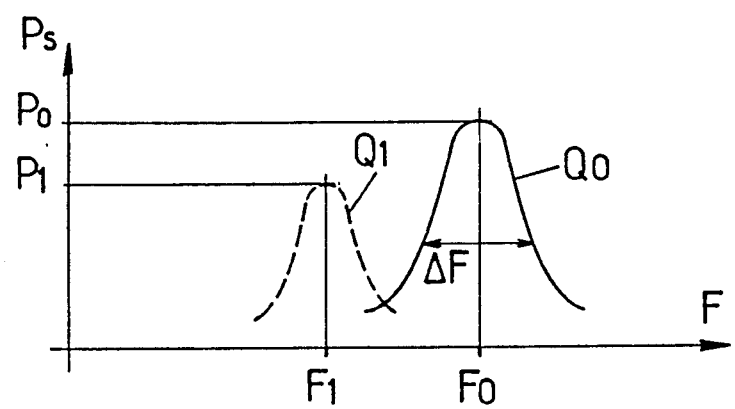
FIG. 4 shows by way of example the variation of the output power of a resonator of the kind illustrated in FIG. 1 as a function of the frequency, when the resonator is empty (continuous line curve) and when it is coupled to a sample (broken line curve)

FIG. 3 shows an arrangement for obtaining such localization of the coupling. In FIG. 3, where the elements corresponding to those of FIGS. 1 and 2 are designated by the same reference number, the ground conducting plane 6 is deformed in the zone of the gap. The edges of the microstrip line 20, which define the gap, are each fixed, for example by soldering, to an electrode 30 which passes through a thin plate 32 of insulating material, made for example from molten silica, and spreads out over a substantially flat face of plate 32, on the opposite side to the line. So that the distance between electrodes 30 and sample 34, shown with a chain-dotted line in FIG. 3, remains constant and well defined during measurements at different points, the electrodes are advantageously formed on the bottom of a shallow cavity 36 formed in the flat surface of plate 32. Thus, by maintaining the sample applied against plate 32, a constant distance, for example 10 microns, is obtained between the electrodes and the sample. Spreading-out of the electrode may be over a very small area and especially very little developed in the direction of the loop.

Since the coupling between sample and resonator decreases very rapidly the further away from the electrode, the resolution merges substantially with the surface of the electrodes and may be reduced to about 4 mm$^2$.

In a variant of the invention, the microstrip line is replaced by a triplate line which is differentiated from the structure shown in FIGS. 1 and 2 by the presence of a second metal conducting plane.

The measuring cell which has just been described may be readily adapted to measurement of the photoconductance. For that, it is sufficient to pierce the resonator at the level of the gap of the loop so as to open a path for the passage of a light beam. Such a passage opening 38 is shown with broken lines in FIG. 3. In this embodiment, it is advantageous to give the gap a very small width, which may be as small as a few microns. Thus, very high electric fields are obtained which increase the rate of generation of electron-hole pairs.

The light beam may be brought by an optical fiber 40 from a laser 42.

Before describing the working of the invention, it may be useful to recall the response characteristics of a resonator of the kind according to the invention, similar to those of a closed cavity. If we designate by $P_O$, $Q_O$ and $F_O$, the output power, the coefficient of quality and the resonance frequency of the empty cavity, the presence of a sample will cause the coefficient of quality to vary which takes the value $Q_1$ and we have, for the same input power, the relation $$1/Q_1 - 1/Q_0 = (\sqrt{P_0/P_1} - 1)\Delta F_0$$

where $\Delta F_O$ is the passband at mid-height.

Whatever the parameter it is desired to measure, the procedure used will involve first of all, and once and for all, measurement of the off-load characteristics of the cavity and particularly the measurement of $P_O$, $Q_O$ and $\Delta F_O$.

Subsequently, for each measuring point, after moving sample 34 along plate 32, the power $P_1$ and possibly its variation $dP_1$ will be measured for each measuring point after application of a magnetic field or a light beam.

From the results of the measurements, it is possible, provided that an appropriate choice of the frequency $F_O$ has been made, to derive the local values of the conductivity of the mobility of the carriers, and of the number of carriers.

In the case of conductivity measurement, the working frequency is chosen so as to obtain a relation which is at least approximately proportional between the variation of power consumption in the resonator, so the variation $\delta(1/Q)$ of $1/Q$ and $1/R$ (where R designates the resistance equivalent to the sample in the measuring cell). The electric diagram equivalent to the measuring cell is formed by this resistance R in series with the capacities C of the capacitors each formed by an electrode 30 and the part of the sample which is opposite (the parasite capacity represented by the gap being made negligible by an appropriate choice of the ratio between the thickness of dielectric 18 and the width of the gap).

Calculation shows that the variation of the power consumption (and so the variation $\delta(1/Q)$ depending on whether the resonator contains a sample or not is :
 substantially proportional to $1/R$ for $RC\omega << 1$ ($\omega$ being the angular frequency);
 maximum for $RC\omega \approx 1$;
 substantially proportional to R for $RC\omega << 1$.

The value of $\omega$ will be chosen so as to be in the first or third variation zone. For that, when passing from one sample to another, it may be necessary to change the resonance frequency :
 either by using another resonance mode of the microstrip resonator,
 or by using another resonator.

In the case of electric resistivity measurement mapping, the proportionality between $1/R$ or R and the variation $\Delta(1/Q)$ gives then excellent sensitivity.

The absolute value of the resistivity may be obtained by previous calibration of the resonator with known samples.

When it is desired to measure the mobility by magnetoresistance with application of a magnetic field B, we have, still in one of the above defined conditions :
 $\Delta R/R = \mu^2 \cdot B^2$ The mobility is measured in absolute value.

In the case where it is desired to measure the photoconductance, the same process may be used if a measurement line is used working by reflection. For such a line, the relative variation of the conductivity at the surface of the sample, caused by illumination of the surface, is linked to the photoconductance by the relation:

$$\Delta\sigma/\sigma = [G\tau(\mu_n+\mu_p)]/(n_O\mu_n+p_O\mu_p)$$

where G is the rate of generation of electron-hole pairs, $\tau$ their lifetime, $n_O$ and $p_O$ the initial concentrations of the electrons and of the holes, $\mu_n$ and $\mu_p$ the respective mobilities.

When the same procedure is applied in a cell in accordance with the invention, the use of the resonator increases the detection sensitivity by a factor close to the coefficient of quality, close to 200 for microstrip resonators. It is accordingly possible to improve the resolution and experience has shown that a resolution of 0.25 mm² can be reached with a photoconductance signal which remains usable in the case of an epitaxied GaInAs layer which however has a mediocre generation rate compared with GaAs.

Figure 5:
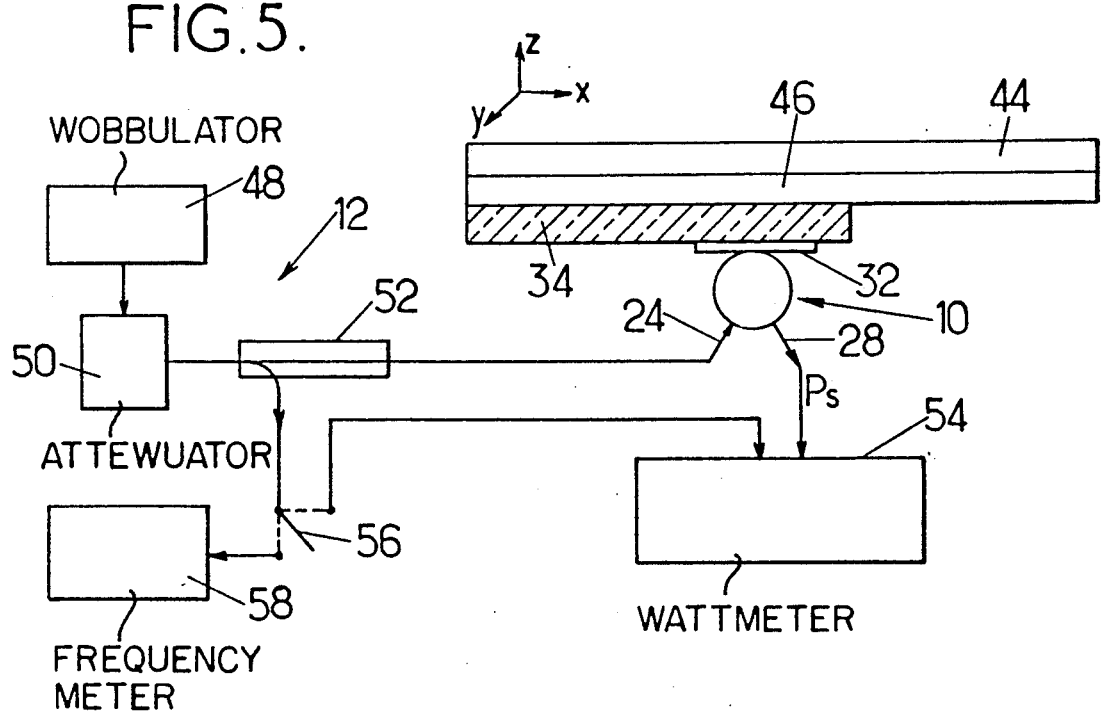
FIG. 5 is a diagram showing the components of a device according to the invention which are added to the measuring cell.

Different circuits associated with the measuring cell may be used and FIG. 5 shows one example. The sample 34 is fixed to a cross motion table 44 from which it is separated by an insulating support 46. Table 44 is provided with means for bringing the sample into mechanical contact with the insulating support 32 belonging to the measuring cell, by moving in direction z (FIG. 5). The sample is then moved in direction x and y by means of the table when it is raised from plate 32 for making a measurement at a new point. The successive movements required may be made automatically, using an automaton of conventional type.

The power supply means 12 for the cell comprise a wobbulator 48 which is connected to the microstrip 24 by an adjustable attenuator 509 and a shunt coupler 52.

The outgoing microstrip 28 is connected to a double wattmeter 54 for measuring both the output power Ps and the power applied to the cell. For this latter measurement, the second input of wattmeter 54 can be connected, by a switch 56, to the shunt output of coupler 52. With the switch, the second output can be oriented at will either towards wattmeter 54 or towards a frequencymeter 58.

By measuring the incident power, it is possible to take into account possible drifts of this power in time and as a function of the frequency. Instead of a double wattmeter 54, it is possible to use a microvoltmeter associated with detection diodes.

The device shown in FIG. 5 must obviously be completed by magnetic field creation means or a light source when it is desired to make electric mobility measurements by magnetoresistance or photoconductance measurements.

We claim:

1. Device for the electric characterization of samples, comprising UHF resonator intended to be coupled locally to said sample, characterized in that said resonator is formed by a microstrip or triplate line loop carried by a conducting plane and having a gap of small length with respect to the length of the loop and means for receiving the sample in a position in which the sample is coupled selectively to the edges of the gap without being interposed therebetween, the edges of the gap of the loop being fixed to two electrodes of small area passing through a thin plate of dielectric material having a flat face for application against the sample.

2. Device according to claim 1, characterized in that the part of the loop remote from the edges of the gap is at a distance from the surface of the thin plate applied on the sample greater than that of the edges, which are fixed directly to the electrodes deposited on the plate.

3. Device according to claim 2, characterized in that the edges of the line which define the gap are each fixed, to an electrode which passes through a thin plate of the insulating material and spreads out over a substantially flat face of the plate, opposite the line.

4. Device according to claim 1, intended for surface homogeneity mapping by photoconductance, characterized in that the resonator comprises a passage which extends through the conducting plane and a dielectric of the line at the level of said gap and which opens between the electrodes.

5. Device according to claim 1, characterized in that the resonator comprises power supply means having a UHF generator driving the resonator through a microstrip having low coupling with the resonator and measuring means comprising a detector connected to a microstrip having, like microstrip, low coupling with the zone of the loop distant from the gap.

6. Device according to claim 1 for use in surface resistivity mapping of a semiconductor, characterized in that the UHF resonator is fed at a frequency such that the product RC $\omega$ is less than 1 or very much greater than 1, R designating the resistance equivalent to the sample in the resonator, C the capacity of the capacitor formed by the edges of the gap and the portion of the facing sample and $\omega$ being the angular frequency.

7. Device according to claim 1 for use in the electric mobility magnetoresistance mapping of semiconductor samples, characterized in that the device comprises means for creating a magnetic field in the measuring zone.

8. Device according to claim 3 wherein said edges of the line which define the gap are fixed by soldering to said electrode.

9. Device according to claim 3 wherein said dielectric material is made from molten silica.

* * * * *